United States Patent [19]

Huss, Jr. et al.

[11] Patent Number: 5,107,048
[45] Date of Patent: Apr. 21, 1992

[54] PROCESS FOR PREPARING LONG CHAIN ALKYL AROMATIC COMPOUNDS EMPLOYING LEWIS ACID-PROMOTED AMORPHOUS INORGANIC OXIDE

[75] Inventors: Albin Huss, Jr., Chadds Ford, Pa.; Quang N. Le, Cherry Hill, N.J.; Samuel A. Tabak, Wenonah, N.J.; Stephen S. Wong, Medford, N.J.

[73] Assignee: Mobil Oil Corp., Fairfax, Va.

[21] Appl. No.: 470,017

[22] Filed: Jan. 25, 1990

[51] Int. Cl.$^5$ .............................. C07C 2/68; C07C 2/70
[52] U.S. Cl. ....................................... 585/456; 585/465
[58] Field of Search ................. 585/456, 459, 460, 462, 585/463, 465, 461

[56] References Cited

U.S. PATENT DOCUMENTS

| | | |
|---|---|---|
| 2,853,533 | 9/1958 | Weaver .............................. 502/231 X |
| 2,939,890 | 6/1960 | Hervert et al. . |
| 3,131,230 | 4/1964 | Hervert et al. . |
| 3,173,965 | 3/1965 | Pappas et al. . |
| 4,035,308 | 7/1977 | Schenach . |
| 4,061,689 | 12/1977 | Ryu et al. ............................. 585/456 |
| 4,094,922 | 6/1978 | Bartek et al. ........................ 585/467 |
| 4,148,834 | 4/1979 | Kennedy et al. . |
| 4,368,342 | 1/1983 | Slaugh ................................... 585/468 |
| 4,431,854 | 2/1984 | Heimlich et al. .................... 585/461 |
| 4,463,207 | 7/1984 | Johnson ............................... 585/462 |
| 4,504,690 | 3/1985 | Forbus ................................. 585/466 |
| 4,530,756 | 7/1985 | Chang et al. ........................ 585/463 |
| 4,691,068 | 9/1987 | Resh . |
| 4,709,110 | 11/1987 | Rodewald ........................... 585/463 |
| 4,731,497 | 3/1988 | Grey .................................... 585/455 |

FOREIGN PATENT DOCUMENTS 1017365  9/1977  Canada ................................. 585/459

Primary Examiner—W. J. Shine
Assistant Examiner—Douglas J. McGinty
Attorney, Agent, or Firm—Alexander J. McKillop; Charles J. Speciale; Dennis P. Santini

[57] ABSTRACT

Aromatic hydrocarbons are alkylated with relatively long chain alkylating agents, e.g., $C_8+$ olefins, at mole ratio of aromatic to alkylating agent of not greater than about 5 in the presence of, as catalyst, a Lewis acid-promoted amorphous, porous inorganic oxide such as silica to provide long chain alkyl aromatic products which are useful, inter alia, as lubricating oil stocks.

17 Claims, 1 Drawing Sheet

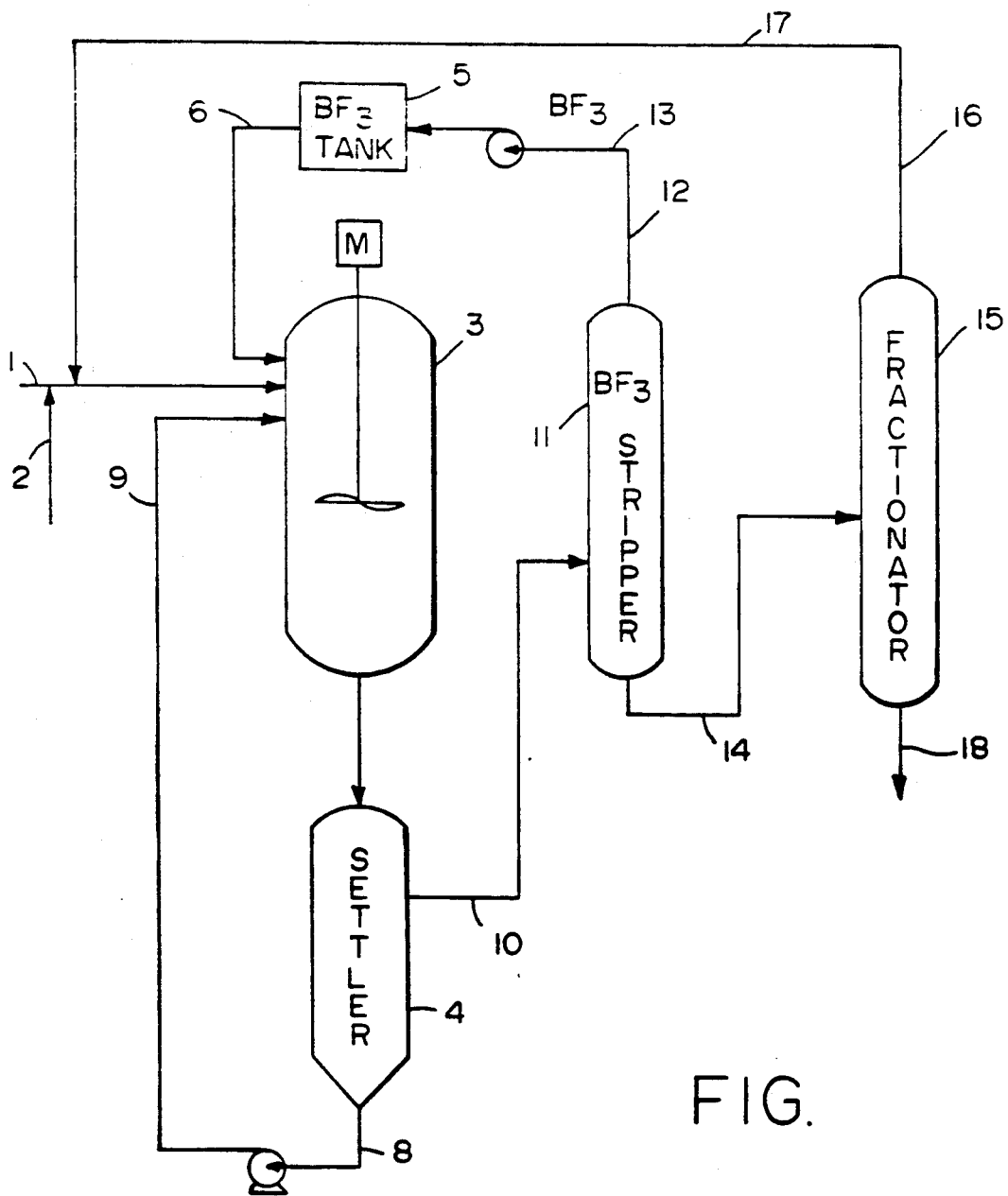
FIG.

PROCESS FOR PREPARING LONG CHAIN ALKYL AROMATIC COMPOUNDS EMPLOYING LEWIS ACID-PROMOTED AMORPHOUS INORGANIC OXIDE

CROSS-REFERENCE TO RELATED APPLICATIONS

This application is related by subject matter to commonly assigned, concurrently filed U.S. patent applications Ser. Nos. 470,012; 469,999; 469,998; 470,015; now U.S. Pat. Nos. 5,030,785; 4,962,256; 4,992,606; and 4,954,663, respectively.

BACKGROUND OF THE INVENTION

This invention relates to a process for preparing long chain alkyl aromatic compounds by alkylating an aromatic compound with a relatively long chain alkylating agent employing Lewis-acid promoted amorphous, porous inorganic oxides as alkylation catalysts.

The alkylation of aromatic hydrocarbon with olefin employing a Lewis acid or Friedel-Crafts catalyst, e.g., $AlCl_3$, $BF_3$, HF, etc., to provide alkyl aromatic compounds is known in the art. Thus, for example, the alkylation processes described in U.S. Pat. Nos. 2,939,890 and 3,131,230 utilize a catalyst composition containing $BF_3$ and a $BF_3$-modified substantially anhydrous inorganic oxide such as anhydrous gamma-alumina. While both patents disclose a molar ratio of aromatic hydrocarbon to olefin of from 2 to 10 or more, and in some cases up to 20, they further disclose that when the olefin alkylating agent is higher in molecular weight than the pentenes, it is particularly necessary to conduct the alkylation process at the higher end of the aforestated range of aromatic to olefin mole ratio. There is, then, an express, specific recommendation against the use of relatively low aromatic to olefin mole ratios in U.S. Pat. Nos. 2,939,890 and 3,131,230 when the olefin (or functionally equivalent alkylating agent) possesses a greater carbon content than the pentenes.

U.S. Pat. No. 3,173,965 discloses the alkylation of benzene with olefin in the presence of a Friedel-Crafts catalyst, e.g., $AlCl_3$, $AlBr_3$, $FeCl_3$, $SnCl_4$, $BF_3$, $ZnCl_2$, HF, $H_2SO_4$, $P_2O_5$ and $H_3PO_4$, to provide a polyalkylated benzene product of relatively high viscosity index (V.I.), i.e., from 90 to 145, which is useful as a lubricant.

According to U.S. Pat. No. 4,035,308, excess benzene is alkylated with decene dimer in the presence of $BF_3$-promoted anhydrous $AlCl_3$ to provide a monoalkyl benzene product useful as a lubricant or power transmission fluid.

U.S. Pat. No. 4,148,834 describes a two-step alkylation process for preparing di-long chain alkyl aromatic compounds, useful as lubricants, in which aromatic hydrocarbon is alkylated with linear monoolefin in the presence of HF catalyst in a first step and aluminum chloride or aluminum bromide catalyst in a second step.

U.S. Pat. No. 4,691,068 discloses the preparation of long chain monoalkyl aromatics useful in producing detergents, employing a Friedel-Crafts catalyst, e.g., $AlCl_3$—HCl, and featuring the recycle of a heavy boiling product fraction to the alkylation reaction.

SUMMARY OF THE INVENTION

It is an object of this invention to provide a process for the alkylation of an aromatic compound with a relatively long chain alkylating agent to provide a long chain alkyl aromatic product employing as alkylation catalyst a Lewis acid-promoted amorphous inorganic oxide.

It is another particular object of the present invention to provide a process for the alkylation of an aromatic hydrocarbon stream, e.g., one containing one or more of benzene, toluene, xylene, naphthalene, and the like, with a relatively long chain alkylating agent to produce an aromatic lube base stock of low pour and cloud point, high viscosity and improved thermal and oxidative stability properties.

By way of realizing the foregoing and other objects of the invention, a process for preparing long chain alkyl aromatic compounds is provided which comprises contacting at least one alkylatable aromatic compound with at least one alkylating agent possessing an alkylating aliphatic group having at least six carbon atoms at a mole ratio of aromatic compound to alkylating agent of not greater than about 5 under alkylation reaction conditions and in the presence of an alkylation catalyst to provide an alkylated aromatic product possessing at least one alkyl group derived from said alkylating agent, said catalyst comprising a Lewis acid-promoted, amorphous, porous inorganic oxide.

Totally contrary to what would be expected from the alkylation processes disclosed in U.S. Pat. Nos. 2,939,890 and 3,131,230 referred to, supra, the alkylation process of this invention not only does not require fairly high aromatic to alkylating agent mole ratios for its effective operation, it actually provides better results in terms of the viscosity index (V.I.) of the resulting lube range product than the same process operated at higher aromatic to olefin mole ratios.

The practical advantages of operating a conversion process at mole ratios of reactants which are closer to the stoichiometric requirements of the conversion will be readily appreciated. Thus, reactors and associated equipment can be smaller in size for an equivalent productivity since a smaller volume of unreacted feedstock need be recycled to the conversion zone. So it is with the alkylation system of the present invention in which recycling of unreacted aromatic is far below that which is required by the alkylation processes of U.S. Pat. Nos. 2,939,890 and 3,131,230.

BRIEF DESCRIPTION OF THE DRAWING

The attached FIGURE of drawing is a block flow diagram illustrating one embodiment of an aromatic alkylation process in accordance with the present invention.

DESCRIPTION OF SPECIFIC EMBODIMENTS

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a hetero atom are also useful provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene and phenanthrene.

Generally the alkyl groups which can be present as substituents on the aromatic compound contain from one to about 22 carbon atoms and preferably from about one to eight carbon atoms, and most preferably from about one to four carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate containing substantial quantities of benzene, toluene and/or xylene constitutes a particularly useful feed for the alkylation process of this invention.

The alkylating agents which are useful in the process of this invention generally include any aliphatic or aromatic organic compound having one or more available alkylating aliphatic groups capable of reaction with the alkylatable aromatic compound. The alkylatable group itself should have at least about 6 carbon atoms, preferably at least about 8, and still more preferably at least about 12 carbon atoms. Examples of suitable alkylating agents are olefins such as hexenes, heptenes, octenes, nonenes, decenes, undecenes, dodecenes, and the like; alcohols (inclusive of monoalcohols, dialcohols, trialcohols, etc.) such as hexanols, heptanols, octanols, nonanols, decanols, undecanols and dodecanols; and alkyl halides such as hexyl chlorides, octyl chlorides, dodecyl chlorides; and, higher homologs of the foregoing. Branched alkylating agents, especially oligomerized olefins such as the trimers, tetramers, pentamers, etc., of light olefins such as ethylene, propylene, the butylenes, etc., are also useful herein.

A wide variety of amorphous, i.e., non-crystalline, porous inorganic oxides are contemplated for use as catalyst herein. These oxides, numerous ones of which are commercially available, include all forms of the oxides of aluminum, silicon, germanium, titanium, zirconium, and the like, and/or other catalytically active amorphous, porous inorganic oxides. Thus, among the amorphous, porous inorganic oxide alkylation catalysts which can be used herein are alumina, silica, germania, titania, zirconia, silica-alumina, titania-alumina, titania-silica, titania-magnesia, titania-zirconia, titania-thoria, titania-beryllia, silica-alumina-titania, silica-alumina-germania, titania-silica-thoria, etc. Of the foregoing, silica, mechanical mixtures of silica and one or more other metal oxides, silicon-containing multimetallic oxides and silicon-containing mixed metal oxides are preferred for use herein.

The inorganic oxide alkylation catalyst herein is promoted by a Lewis acid, generally considered to be a molecule which is capable of combining with another molecule or ion by forming a covalent chemical bond with two electrons from the second molecule or ion. Thus, a Lewis acid functions as an electron acceptor. Examples of Lewis acids include boron trifluoride ($BF_3$), antimony pentafluoride ($SbF_5$) and aluminum chloride ($AlCl_3$). The present invention contemplates the use of these and all other Lewis acids including those disclosed in "Friedel-Crafts and Related Reactions", Interscience Publishers, Chapters III and IV (1963), the contents of which are incorporated by reference herein. $BF_3$ is a preferred Lewis acid for use in the alkylation process of this invention. In the case of $BF_3$, this promoter is preferably present in the alkylation zone in an amount which exceeds that required to saturate the inorganic oxide catalyst component. The inorganic oxide can be combined with the Lewis acid promoter prior to introduction of the former into the conversion zone of the reactor. However, in a preferred embodiment, the inorganic oxide is combined with the Lewis acid, specifically $BF_3$, within the reaction zone.

The alkylation process of this invention is conducted such that the organic reactants, i.e., the alkylatable aromatic compound and the alkylating agent, are brought into contact with the Lewis acid-promoted inorganic oxide catalyst in a suitable reaction zone such as, for example, in a flow reactor containing a fixed bed of the catalyst composition, under effective alkylation conditions at an aromatic compound to alkylating agent mole ratio of not greater than about 5:1 and preferably less than about 2:1. Aside from the aromatic compound to alkylating agent ratio, the other conversion conditions are not particularly critical and include a temperature of from about $-40°$ C. to about 250° C., a pressure of from about 0.2 to about 250 atmospheres and a feed weight hourly space velocity (WHSV) based on the total weight of Lewis acid-promoted catalyst of from about 0.01 to about 500 $hr^{-1}$. Preferred reaction conditions include a temperature of from about $-20°$ C. to about 150° C., a pressure of from about 1 to about 25 atmospheres and a WHSV of from about 0.1 to about 100 $hr^{-1}$. The reactants can be in either the vapor phase or the liquid phase and can be neat, i.e., free from intentional admixture or dilution with other material, or they can be brought into contact with the catalyst composition with the aid of carrier gases or diluents such as, for example, hydrogen or nitrogen.

The alkylation process herein can be carried out as a batch-type, semi-continuous or continuous operation utilizing a fixed or moving bed catalyst system. A preferred embodiment entails use of a catalyst zone wherein the hydrocarbon charge is passed concurrently or countercurrently through a moving bed of particle-form catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

It can be advantageous to add water to the alkylation reactor, e.g., at a rate of from about 0.1 ppmw to about 1 wt %, based upon total hydrocarbon feed rate, preferably at a rate of from about 0.1 ppmw to about 500 ppmw. The water can be supplied as such or as a feed material which produces water under the alkylation conditions selected. Suitable water-producing materials which can be introduced into the reactor without interfering with the desired alkylation include monohydric and dihydric alcohols which yield water upon undergoing dehydration. Of this group, particular preference is accorded the aliphatic alcohols, especially those containing 1 to 6 carbon atoms as, for example, methanol, ethanol, isopropanol, t-butyl alcohol and isopentyl alcohol. The optional water and/or water-producing material can be added directly to the reactor, e.g., with the feed, and/or it can be incorporated into the catalyst, either by direct contact therewith or by exposing the catalyst to an atmosphere of water and/or water-producing material. For example, when the added water and/or water-producing material is pre-introduced into the catalyst, the amount of water and/or water-producing material taken up by the catalyst can be made to vary from about 0.5 to about 25, and preferably from about 1 to about 10, weight percent thereof.

A suitable system for carrying out the aromatic alkylation process of this invention on a continuous basis is shown in the FIGURE of drawing. A stream containing benzene and $C_{16}$ alpha olefin is introduced through line 1 into stirred reactor 3 containing silica. Optionally, water and/or a water-producing material such as methanol is introduced through line 2 into the reactor. $BF_3$ is introduced as needed from holding tank 5 through line 6 into the reactor. The amount of $BF_3$ introduced is such as to exceed that which is required to saturate the silica. Catalyst slurry is removed from the reactor and is introduced to settling vessel 4, the recovered silica thereafter being recycled to the alkylation reactor via line 9. The hydrocarbon product mixture is removed from the settling vessel through line 10 and introduced into $BF_3$ stripper 11 from which $BF_3$ is removed as overhead through line 12 and recycled through line 13 to $BF_3$ holding tank 5. The remaining hydrocarbon product mixture is withdrawn from the $BF_3$ stripper and passes through line 14 into fractionator 15 where unreacted $C_{16}$ alpha olefin is removed as overhead through line 16 and recycled through line 17 to reactant feed stream line 1. Desired alkylated benzene product is withdrawn from the bottom of fractionator 15 through line 18.

The following examples are illustrative of the alkylation process herein.

EXAMPLE 1

This example illustrates the use of $BF_3$-promoted silica to alkylate toluene with $C_{16}$ alpha olefin at a mole ratio of toluene to olefin of 5:1.

The alkylation was carried out in a 300 cc autoclave reactor operating at 20° C. and 200 psig and containing 10 g silica with continuous addition of $BF_3$. The toluene/olefin feed was continuously introduced into the reactor at a rate of 100 cc/hr and product was continuously withdrawn therefrom. Under these conditions, complete conversion of the $C_{16}$ alpha olefin was observed. The product was distilled to separate the unreacted toluene. Analyses of the resulting lube range product, which appeared to be free of any olefin oligomer(s), indicated the product to be made up of a mixture of mono-alkylated toluene (90 wt. %) and dialkylated toluene (10 wt. %)

The properties of the 600° F.+ lube range material and those of the 600°–800° F. monoalkylated toluene fraction thereof are set forth in Table I as follows:

TABLE I

| Properties of Aromatic Lube Product | | |
|---|---|---|
| Lube Properties | | |
| Boiling Point, °F. | 600+ | 600–800 |
| Pour Point, °F. | −20 | −25 |
| KV at 40° C., cSt | 11.0 | 9.09 |
| KV at 100° C., cSt | 2.87 | 2.68 |
| VI | 108 | 140 |

EXAMPLE 2

Example 1 was substantially repeated but employing bezene as the alkylatable aromatic reactant at a benzene to $C_{16}$ alpha olefin mole ratio of 5:1. The properties of the resulting 600° F.+ lube range alkylate product are set forth in Table II as follows:

TABLE II

| Properties of Aromatic Lube Product | |
|---|---|
| Lube Properties | |
| Boiling Point, °F. | 600+ |
| Pour Point, °F. | 0 |
| KV at 40° C., cSt | 10.1 |
| KV at 100° C., cSt | 2.79 |
| VI | 121 |

As these data show, the resulting 600° F.+ lube range product has a higher VI than the corresponding 600° F.+ material produced with the toluene/$C_{16}$ alpha olefin feed of Example 1.

EXAMPLE 3

Example 2 was substantially repeated but at a benzene to $C_{16}$ alpha olefin mole ratio of 1:1. The properties of the resulting 600° F.+ lube range alkylate product are set forth in Table III as follows:

TABLE III

| Properties of Aromatic Lube Product | |
|---|---|
| Lube Properties | |
| Boiling Point, °F. | 600+ |
| Pour Point, °F. | +10 |
| KV at 40° C., cSt | 14.2 |
| KV at 100° C., cSt | 3.58 |
| VI | 138 |

As these data show, the VI of the resulting 600° F.+ lube range product is better than that of the lube product of Example 2. Analyses indicated that even at the low aromatic:olefin mole ratio of this example, no olefin oligomer appears to have been produced.

What is claimed is:

1. A process for preparing a long chain alkyl aromatic compound which comprises contacting at least one alkylatable aromatic compound with at least one alkylating agent possessing an alkylating aliphatic group having at least six carbon atoms in a stirred reactor at a mole ratio of aromatic compound to alkylating agent of not greater than about 2 under alkylation reaction conditions and in the presence of an alkylation catalyst to provide an alkylated aromatic product possessing at least one alkyl group derived from said alkylating agent, said catalyst comprising a Lewis acid-promoted amorphous, porous inorganic oxide, wherein said Lewis acid is $BF_3$.

2. The process of claim 1 wherein the mole ratio of aromatic compound to alkylating agent is about 1.

3. The process of claim 1 wherein the inorganic oxide contains at least one element selected from the group consisting of aluminum, silicon, germanium, titanium and zirconium.

4. The process of claim 1 wherein the inorganic oxide comprises a silicon-containing oxide.

5. The process of claim 1 wherein the inorganic oxide comprises silica.

6. The process of claim 1 wherein the mole ratio of aromatic compound to alkylating agent is about 1, and the inorganic oxide contains at least one element selected from the group consisting of aluminum, silicon, germanium, titanium and zirconium.

7. The process of claim 1 wherein the mole ratio of aromatic compound to alkylating agent is about 1, and the inorganic oxide comprises silica.

8. The process of claim 1 wherein the alkylation is carried out in the presence of small amounts of water and/or other material which produces water under alkylation reaction conditions.

9. The process of claim 1 wherein the alkylating aliphatic group contains at least about 8 carbon atoms.

10. The process of claim 1 wherein the alkylating aliphatic group contains at least about 12 carbon atoms.

11. The process of claim 1 wherein the alkylating agent is an olefin.

12. The process of claim 1 wherein the alkylating agent is an alcohol.

13. The process of claim 1 wherein the alkylating agent is an alkyl halide.

14. The process of claim 1 wherein the alkylatable aromatic compound is selected from the group consisting of benzene, xylene, toluene and 1,2,3,5-tetramethylbenzene.

15. The process of claim 1 wherein the alkylatable aromatic compound is selected from the group consisting of naphthalene, anthracene, naphthacene, perylene, coronene and phenanthrene.

16. The process of claim 1 wherein the alkylation reaction conditions include a temperature of from about $-40°$ C. to about $250°$ C., a pressure of from about 0.2 to about 250 atmospheres and an WHSV of from about 0.01 to 500 $hr^{-1}$.

17. The process of claim 1 wherein the alkylation reaction conditions include a temperature of from about $-20°$ C. to $150°$ C., a pressure of from about 1 to about 25 atmospheres and a WHSV of from about 0.1 to about 100 $hr^{-1}$.

* * * * *